United States Patent [19]

Mendenhall

[11] Patent Number: 4,606,807
[45] Date of Patent: Aug. 19, 1986

[54] PROBE FOR MEASURING THE CARBON POTENTIAL OF ENDOTHERMIC GAS

[76] Inventor: Donald H. Mendenhall, 1422 SW. 143rd, Seattle, Wash. 98166

[21] Appl. No.: 738,166

[22] Filed: May 24, 1985

Related U.S. Application Data

[63] Continuation-in-part of Ser. No. 547,742, Nov. 11, 1983, abandoned.

[51] Int. Cl.⁴ .............................................. G01N 27/46
[52] U.S. Cl. .................................... 204/433; 204/408; 204/409; 204/424; 204/427; 204/1 T
[58] Field of Search ............... 204/1 S, 421–429, 204/433, 408, 409

[56] References Cited

U.S. PATENT DOCUMENTS

| | | | |
|---|---|---|---|
| 3,597,345 | 8/1971 | Hickam et al. | 204/427 |
| 3,598,711 | 8/1971 | Flais | 204/427 |
| 3,699,032 | 10/1972 | Rapp | 204/1 S |
| 4,005,001 | 1/1977 | Pebler | 204/426 |
| 4,098,650 | 7/1978 | Sayles | 204/427 |
| 4,115,229 | 9/1978 | Capone | 204/1 S |
| 4,175,019 | 11/1979 | Murphy | 204/429 |
| 4,184,934 | 1/1980 | Bode et al. | 204/428 |
| 4,247,380 | 1/1981 | McIntyre | 204/1 S |
| 4,339,318 | 7/1982 | Tanaka et al. | 204/428 |
| 4,430,192 | 2/1984 | Maeda | 204/428 |

OTHER PUBLICATIONS

Ametek Bulletin, p. 64, (1983).

*Primary Examiner*—T. Tung
*Attorney, Agent, or Firm*—Seed and Berry

[57] ABSTRACT

An oxygen probe for measuring the carbon potential of endothermic gas in a heat treating furnace. The probe uses a readily available, automative-type oxygen sensor having a solid electrolyte element. The sensor is mounted on a heat conducting base plate. The sensor element is surrounded by a gas flow tube extending from the base plate. Exit ports around the base of the sensor element extend through the base plate and into the area defined by the gas flow tube causing an axial, radially symmetric flow of gas around the sensor element. The tip of the element is heated above the temperature of the gas while the base of the element is conductively cooled by the base plate. A temperature gradient is thus caused along the length of the sensor element, increasing its sensitivity.

10 Claims, 3 Drawing Figures

4,606,807

PROBE FOR MEASURING THE CARBON POTENTIAL OF ENDOTHERMIC GAS

CROSS-REFERENCE TO RELATED APPLICATION

This application is a continuation-in-part of U.S. Ser. No. 547,742, filed Nov. 11, 1983, now abandoned.

TECHNICAL FIELD

The present invention relates to an oxygen probe for measuring the carbon potential of endothermic gas exiting a steel heat treating furnace.

BACKGROUND ART

When heat treating carbon steels, such as during case hardening or neutral hardening, the steel is placed in a heated treating furnace, and endothermic gas, which is rich in carbon monoxide and carbon dioxide, is slowly circulated through the furnace to protect the steel. Because the properties of the steel depend in part upon the nature of the gas within the furnace, it is important to know and monitor the carbon potential of this endothermic gas so that the proper treating is achieved. It is well known that the carbon potential of a gas is related to the partial pressure of oxygen in the gas. Thus, oxygen sensors can be used to monitor the carbon potential of endothermic gases.

A variety of devices are presently available for measuring the partial pressure of oxygen in a gas relative to a reference gas. Some of these devices are adapted for use in determining the oxygen content of gases in a furnace or flue wall. Typical devices are described in U.S. Pat. Nos. 4,339,318, to Tanaka et al.; 4,005,001, to Pebler; 3,699,032, to Rapp; 4,115,229, to Capone; 4,098,650, to Sayles; 4,247,380, to McIntyre; 3,598,711, to Flais; 3,597,345, to Hickam; and 4,430,192, to Maeda. These devices employ an oxygen sensor having a solid electrolyte sensor element which generates an electric potential which is proportional to the differential partial pressures of oxygen on two sides of the sensor element. By sensing the oxygen concentration on one side of the sensor element relative to ambient air on the other side of the element, those skilled in the relevant art can easily determine the constituent compositions of the gas being measured. Thus, similar devices disclosed in Bulletin P-64 and Bulletin P-82 of Ametek Corporation, a division of Thermox Instruments, are capable of analyzing the carbon potentials of gases utilizing these oxygen sensors.

Most of these devices, however, utilize custom-made, solid electrolyte sensor elements of the zirconium oxide type, which are relatively large and therefore expensive. Furthermore, since the sensors are not mass-produced, their cost is often prohibitive. If the sensor element fails for any reason, it is typically returned to the factory for renewal rather than replacement, thus resulting in substantial downtime while waiting for a replacement.

In addition to the expense of the sensor elements discussed, a number of problems have been discovered when using the above-type devices in heat treating furnace applications. The devices tend to clog up with soot deposits which require the removal of the element and the cleaning of the related apparatus. This is often very difficult with the above devices and subjects the relatively delicate and expensive sensor element to the possibility of breakage.

In different contexts, it has been known that oxygen sensors having zirconium oxide elements may be used to measure the oxygen content of exhaust gases in an internal-combustion engine. These sensors are made from the same type of materials as the above-discussed sensors, but are much shorter in length so as to fit radially into an automobile exhaust. These sensors have been mass-produced for the automotive market. Typical of these sensors is the type disclosed in U.S. Pat. Nos. 3,844,920, to Burgett, et al., 4,175,019, to Murphy, and 4,184,934, to Bode, et al. A sensor of this type is mass-producible and is presently being mass-produced by General Motors. The sensor is less expensive than the previously discussed sensors. However, due to the smaller size of the zirconium oxide elements, sensors of this type require a highly symmetrical flow pattern to achieve repeatable outputs for a given gas chemistry. The sensors are thus more susceptible to variations in flow patterns and for this reason are not well adapted for use in heat treating furnaces for measuring the carbon potential of endothermic heat treating gases. It would be desirable to utilize the less expensive and mass-produced-type electrolyte oxygen sensor to measure the carbon potential of endothermic gases in heat treating furnaces. However, the disadvantages associated with this smaller type of sensor has precluded its use in the industry.

Thus, a need exists for an oxygen probe attachable to an auxiliary outlet of a heat treating furnace for measuring the carbon potential of endothermic heat treating gas within the furnace utilizing mass-produced zirconium oxide electrolyte sensors.

DISCLOSURE OF THE INVENTION

It is an object of the present invention to provide an oxygen probe for measuring the carbon potential of endothermic gases which utilizes a relatively inexpensive, replaceable zirconium oxide electrolyte sensor.

It is also an object of the invention to provide a probe for measuring the carbon potential of endothermic gases which resists sooting in the area around the sensor element.

It is yet another object of the invention to provide a probe for measuring the carbon potential of endothermic gases which has an easily removable sensor facilitating the cleaning of the probe should soot deposits occur.

The invention achieves these objects by providing a probe which utilizes a relatively inexpensive, replaceable oxygen sensor of the type used in automotive applications. The probe provides for a uniform, axial, and generally radially symmetrical flow of endothermic gas around the sensor element to improve the accuracy of the sensor. The probe causes a temperature gradient to appear across the longitudinal dimension of the sensor element to boost the voltage output of the sensor for a given carbon potential in the gas, thus providing an enlarged measuring range for carbon potentials. The device further comprises a heater which maintains the tip of the element at a temperature which is always greater than the temperature of the endothermic gas entering the probe to maintain the accuracy of the readings from the relatively short sensor element.

The probe has a heat-conducting base plate having a threaded aperture sized to accept a typical automotive oxygen sensor. The sensor has a relatively short electrolytic element, typically about one inch long. Because of the relatively short length of the sensor element, an accurate and even flow path for endothermic gas around the sensor is required for accurate readings. The base plate has a plurality of exit ports surrounding the aperture for venting endothermic gas away from the base of the sensor element. The sensor element and the exit ports are enclosed by a longitudinally extending gas flow tube connected at one end to the base plate. The gas flow tube encloses the sensor element and the exit ports so that the endothermic gas flows axially over the sensor element and out through the exit ports. Preferably, four evenly spaced exit ports are provided, causing a radially symmetrical and axial flow of gas over the sensor. It has been found that this flow configuration causes accurate and repeatable measurements to be made with this type of sensor.

It has also been found that temperature control of this type of sensor element is much more critical than for other types of sensors. The probe is provided with an annular heater which surrounds the gas flow tube. The heater is approximately twice as long as the sensor element and abuts the base plate so that the tip of the sensor is approximately at the midpoint of the heater and thus the hottest point in the gas flow tube. An annular ceramic fiber gasket is placed between the base plate and the annular heater to prevent the annular heater from transferring heat to the base plate. A temperature gradient is thereby established from the tip of the sensor element to the base of the sensor element. It has been found that this temperature gradient greatly increases the voltage output of the sensor for a given potential in the endothermic gas. Thus, the scale for carbon potentials measured by the sensor is greatly expanded, even though the sensor being used has a relatively small electrolytic sensor element.

The temperature of the tip is controlled by a thermocouple which measures the temperature at the interface between the inner surface of the heater and the outer wall of the gas flow tube and the midpoint of the heater. Thus, accurate control of the sensor element tip temperature can be maintained.

The configuration of the probe lends itself to relatively simple cleaning of the gas flow tube should sooting occur in the tube. To clean the tube, the oxygen sensor is unscrewed from the base plate and a brush is inserted into the tube to remove the soot. The sensor is then replaced for operation of the probe.

To reduce sooting in the tube, a coil of high nickel content wire is inserted into the gas flow tube against the inner wall thereof. It is known that the nickel contents of the wire causes a catalytic reaction in the endothermic gas, reducing soot deposits in the tube. By coiling the wire within the tube, the surface area of available catalyst is greatly increased as compared to a solid nickel gas flow tube or a nickel-plated tube. Thus, the catalytic reaction is more complete and sooting is even further reduced. The gas flow tube is provided with a threaded end for attaching the probe to an outlet of a heat treating furnace.

Typically, the amount of sample gas flowing through the probe will be on the order of 2 to 6 cubic feet per hour, while the amount of endothermic gas flowing through the furnace is on the order of 500 to 800 cubic feet per hour.

This simple economical structure is a decided step forward in the art in that the probe utilizes a relatively inexpensive zirconium oxide-type oxygen sensor which is readily available as a standard automotive part. The probe is designed to increase the performance of the off-the-shelf sensor so that it is usable as part of a carbon potential probe for endothermic gases.

BEST MODE FOR CARRYING OUT THE INVENTION

Figure 1:
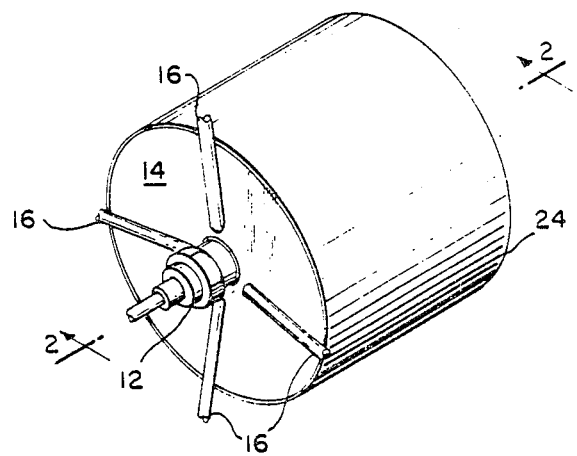
FIG. 1 is an isometric view of the oxygen probe of the present invention.
Figure 2:
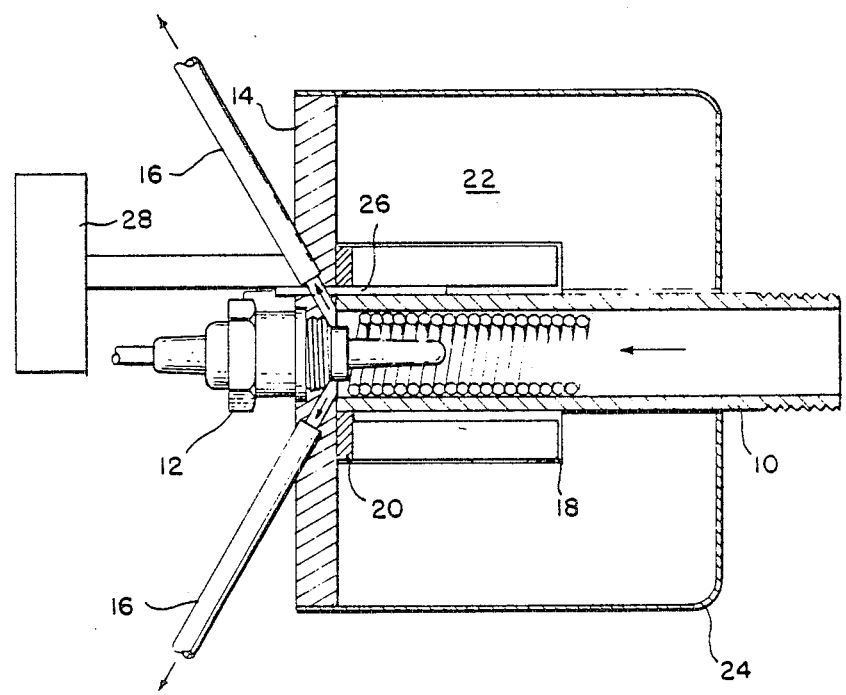
FIG. 2 is an enlarged, cross-sectional view taken generally along line 2—2 of FIG. 1.

The oxygen probe of the present invention includes a gas flow tube 10 which can be threaded into an auxiliary outlet of a steel heat treating furnace. The gas flow tube defines a flow path for a sample volume of exiting endothermic gas. Typically, the probe will sample 2 to 6 cubic feet per hour of endothermic gas while 500 to 800 cubic feet per hour are flowing through the heat treating furnace.

At the far end of the tube 10, a zirconium oxide sensor 12 screws into a base plate 14 attached to the end of the tube. The zirconium oxide sensor is typically of the type disclosed in U.S. Pat. No. 3,844,920, to Burgett, et al. It has been found that a readily available sensor is part No. AFS5P, manufactured by the A.C. Spark Plug Division of General Motors. This sensor is presently used on General Motors automobiles to sense the oxygen content of exhaust gases in automobiles, and is readily available from GM service dealers at a relatively low price.

The zirconium oxide sensor 12 is positioned substantially along the longitudinal axis of the tube 10. A plurality of exit ports 16 extend angularly through the base plate 14 and terminate near the base of the sensor element 17. The exit ports communicate with the gas flow tube allowing endothermic gas to exit the tube at the base of the sensor element. Generally, there are four evenly spaced exit ports 16, but fewer may be used if a generally evenly developed, radially symetrical flow passes by the sensor element 17. It has been found that at least two ports must be used to achieve consistent readings from the probe. When four evenly spaced exit ports are provided, the flow of endothermic gas around the sensor element 17 is generally axial over the outer surface of the sensor element and radially symmetrical around the sensor element due to the positioning of the exit ports.

The sensor element 17 is typically hollow at its base and closed at its tip. The inner surface of the sensor element 17 is exposed to ambient air from a reference port 19, which passes through the threaded portion 21 of the sensor to the element. The ambient air serves as a reference gas for the sensor 12. The difference in the partial pressure of oxygen in the endothermic gas flowing over the outer surface of the sensor element and the partial pressure of oxygen in the reference gas causes a potential difference between the surfaces of the element in proportion to the carbon potential of the endothermic gas.

The sensor element 17 is maintained at a relatively constant temperature by an annular heater 18 which surrounds the tube 10 in the vicinity of the sensor element. A ceramic fiber gasket 20 insulates the heater 18 from the base plate 14 while a sheathing of insulation 22 surrounds the annular heater 18 and covers the otherwise exposed end of the heater. This insulation layer 22 is encased in a case 24 of aluminum or another suitable material. The annular heater has a length equal to approximately twice the length of the sensor element 17. This places the tip of the sensor element at approximately the midpoint of the heater. Thus, the tip of the element is in a radial plane which passes through the center of the heater at the hottest point in the gas flow tube 10.

The base plate 14, threadedly receives the sensor 12 in a heat conducting relation. The base plate is sufficiently massive to serve as a heat sink for the sensor. The base plate also has a relatively large surface area exposed to the ambient air. The base plate is thus capable of conducting heat away from the base of the sensor element 17 through the threaded portion 21 and radiating the heat to the ambient air. The base plate 14 is insulated from the heater 18 by the gasket 20 so that the base plate remains cooler than the tip of the sensor element. A temperature gradient is therefore created between the tip of the sensor element and the base thereof. It has been found that this temperature gradient greatly increases the range of voltage output for the sensor element, therefore increasing the accuracy and sensitivity of the sensor 12. Without this increase in sensor sensitivity, the range of outputs which a sensor of the type utilized would typically provide would be insufficient for measuring the carbon potential of endothermic gases.

The temperature of the annular heater 18 is maintained by measuring the temperature of the heater with a thermocouple 26 which is positioned between the heater 18 and the outside of the tube 10 in a bore which passes through the plate 14. The thermocouple is located at the midpoint of the heater to control the temperature of the tip of the sensor element. Generally, the thermocouple is a Chromel-Alumel ISA Type K thermocouple, which is connected to a suitable controller 28.

The controller 28 monitors the electrical signal generated by the thermocouple 26 and generates a proportional electric signal to power the annular heater 18. In this fashion, minor changes in the temperature of the annular heater 18 can be immediately detected and corrected. A suitable 335-watt, 67.5-volt heater 18 is available from Thermcraft. A heater of this type is easily controllable to create a constant heat which allows the temperature of the tip of the sensor element to be regulated between about 900°-2000° F., and preferably, about 1400° F.

To avoid condensation of water, it is also important that the tube 10 be as short as possible so that the gas remains hot prior to reaching the sensor element. It is generally preferred to operate the tip of the sensor element at a temperature which is above the expected temperature of the sample endothermic gas leaving the heat treating furnace. It has been found that a tip temperature which is lower than the temperature of the exiting gas leads to inconsistent and unrepeatable readings.

Figure 3:
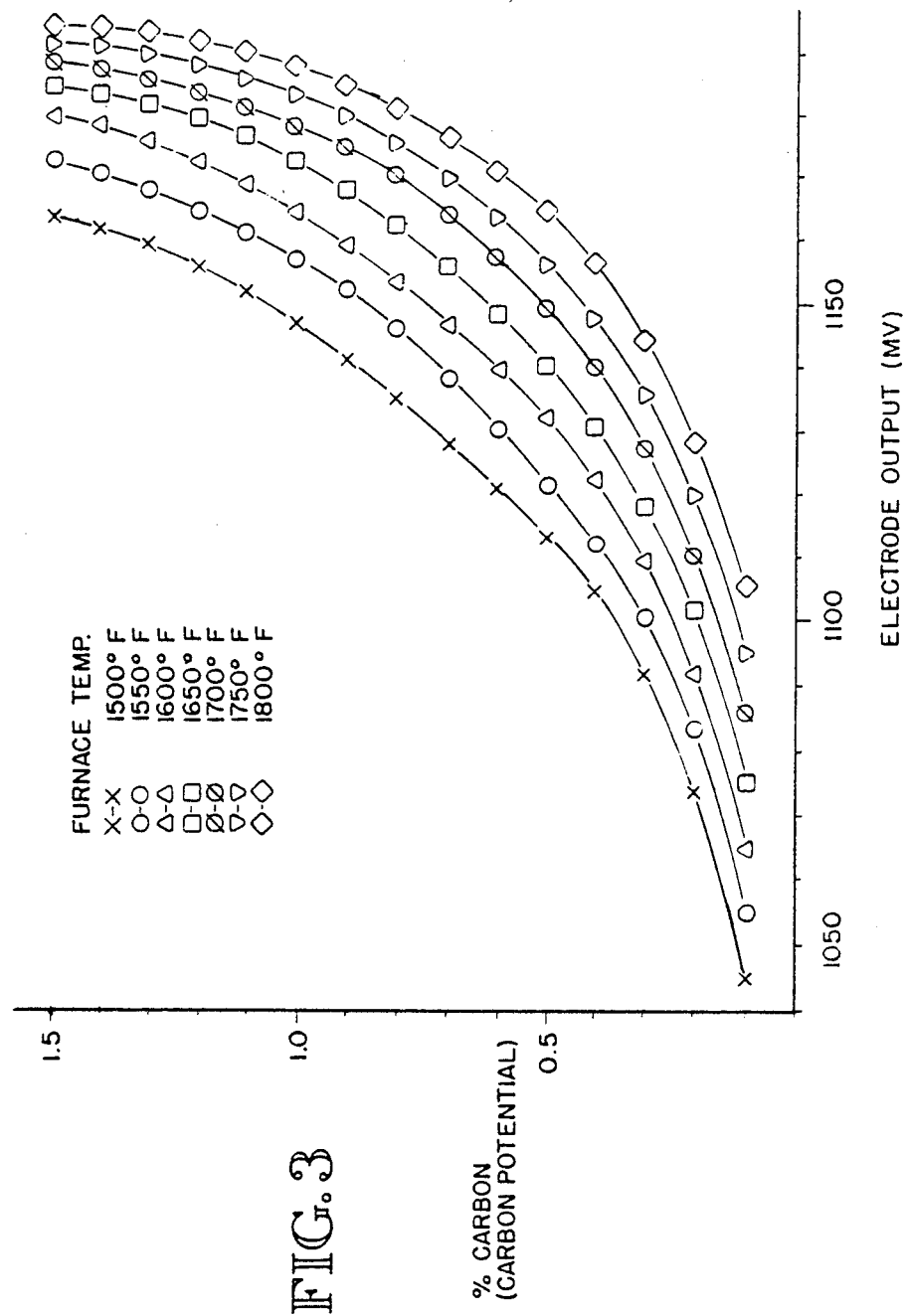
FIG. 3 is a graph of the carbon potential of the endothermic gas versus the sensor output in millivolts of the oxygen probe of the present invention.

A correlation of the electrical output of the preferred probe corresponding to a known carbon potential is shown in tabular form and is graphically represented in FIG. 3 for flows of endothermic gas at between about 2 to 6 cubic feet per hour (usually 3 to 4 cubic feet per hour).

TABLE I

Correlation of ZrO Electrode Output (mV) Versus % Carbon in Endothermic Gas for Various Furnace Temperatures

| % C | Electrode Output (mV) | | | | | | |
|---|---|---|---|---|---|---|---|
| CARBON POTENTIAL | | | | | | | |
| 1.54 | 1163 | 1171 | 1178 | 1183 | 1187 | 1191 | 1192 |
| 1.4 | 1161 | 1169 | 1176 | 1181 | 1185 | 1190 | 1191 |
| 1.3 | 1158 | 1166 | 1174 | 1179 | 1183 | 1188 | 1190 |
| 1.2 | 1154 | 1163 | 1171 | 1177 | 1181 | 1186 | 1171 |
| 1.1 | 1150 | 1159 | 1167 | 1174 | 1179 | 1184 | 1187 |
| 1.0 | 1145 | 1155 | 1163 | 1170 | 1176 | 1181 | 1185 |
| 0.9 | 1140 | 1150 | 1158 | 1166 | 1173 | 1188 | 1182 |
| 0.8 | 1134 | 1144 | 1153 | 1161 | 1168 | 1174 | 1179 |
| 0.7 | 1128 | 1137 | 1146 | 1155 | 1162 | 1169 | 1175 |
| 0.6 | 1121 | 1130 | 1139 | 1148 | 1156 | 1163 | 1170 |
| 0.5 | 1113 | 1122 | 1131 | 1139 | 1147 | 1155 | 1163 |
| 0.4 | 1105 | 1114 | 1122 | 1131 | 1139 | 1147 | 1155 |
| 0.3 | 1092 | 1101 | 1109 | 1118 | 1127 | 1136 | 1144 |
| 0.2 | 1070 | 1080 | 1090 | 1100 | 1010 | 1019 | 1126 |
| 0.1 | 1045 | 1055 | 1065 | 1075 | 1085 | 1095 | 1105 |
| Furnace Temp. °F. | 1500 | 1550 | 1600 | 1650 | 1700 | 1750 | 1800 |

The structure of the probe as described allows for easy cleaning of the probe should soot deposits appear within the gas flow tube 10. To clean the tube of soot deposits, one only need unscrew the sensor 12 and run a brush through the tube. To again operate the probe, the sensor is simply threaded back in place.

It has been found that by providing a nickel catalyzing agent inside the gas flow tube, sooting within the gas flow tube can be reduced. One method for reducing the sooting in the gas flow tube is to construct the tube from Inconel material, which has a naturally high nickel content. A preferred method is to insert a coil of 16-gauge, 80% nickel, 20% chrome wire 30 into the gas flow tube. The coil is rotatably urged into the tube by rotating the coil in the direction tending to wind the coil. Once in the gas flow tube, the coil will partially unwind and hold itself against the inner wall of the tube. The sensor 12 is then threaded into place for operation of the probe.

It has been found that the increased surface area of catalyzing agent exposed to the endothermic gas sample provided by the coil geometry greatly reduces sooting in the gas flow tube as compared to an Inconel gas flow tube, thus increasing the service period required between cleanings. A uniform reduction in voltage output from the sensor 12 generally indicates a soot buildup in the gas flow tube, and observation of this phenomena indicates that cleaning of the tube is necessary.

The invention achieves a significant advantage in that the removal of the sensor for cleaning purposes is relatively easy. Furthermore, if the sensor fails for any reason, a replacement sensor is readily available at a reasonable price from most GM dealers. Thus, downtime is minimal. Because of the relatively low cost of the sensor, the risk involved in cleaning the tube is not great. Therefore, the user is encouraged to maintain the tube, thereby increasing the accuracy of the probe over other probes.

While a preferred embodiment of the present invention has been shown and described, those skilled in the art will readily recognize modifications that might be made to the invention without departing from its inventive concept. Therefore, the claims should be construed liberally in light of this description and should be limited only as is necessary in light of the pertinent prior art.

While described in terms of its preferred use to measure the carbon potential of endothermic gas, the probe of the present invention may also be used to measure the products of combustion of fossil fuels on natural gas, oil, or coal burners where it is important to monitor the excess air fed to the burner. Those skilled in the art will also recognize other uses for the probe.

I claim:

1. An oxygen probe attachable to an auxiliary outlet of a heat treating furnace for measuring the carbon potential of endothermic heat treating gas within the furnace, comprising:
   a replaceable oxygen sensor having an elongated, solid electrolyte element, the element being hollow at a base end and closed at the tip, the base of the element supported by a threaded portion on the sensor, the inner surface of the element being exposable to a reference gas and the outer surface of the element being exposable to the endothermic gas to be measured such that an electric potential is generated between the surfaces of the element in proportion to the carbon potential of the measured endothermic gas;
   a base plate defining an aperture around the threaded portion of the sensor so that the sensor element protrudes through the aperture, the base plate having at least two substantially diametrically opposed exit ports extending through the base plate, and radially spaced from the center of the aperture for venting endothermic gas away from the base of the sensor element;
   a gas flow tube connected by one of its ends to the base plate and substantially coaxially aligned with the sensor element, the inner wall of the gas flow tube enclosing the sensor element and the exit ports, the other end of the gas flow tube having means for joining the gas flow tube to the auxiliary outlet of the furnace, the gas flow tube and the exit ports causing an axial, substantially radially symmetrical gas flow path around the sensor element for substantially the entire length of the senor element, including means for catalyzing the endothermic gas within the gas flow tube to reduce soot deposits within the tube;
   a controllable annular heater having an inner surface contacting the outer wall of the gas flow tube and having one end towards the base plate and the other end extending therefrom approximately twice the length of the sensor element so that the tip of the sensor element is positioned along the midsection of the heater;
   means for measuring the temperature of the midsection of the heater to determine the temperature of the tip of the sensor element; and
   means for maintaining the measured temperature of the tip of the sensor element greater than the temperature of the endothermic gas entering the gas flow tube.

2. The probe of claim 1, wherein the base plate is in thermally conductive communication with the base of the sensor element and wherein the base plate has a sufficient mass and surface area to conduct heat energy from the base of the sensor element and wherein the probe further includes means for thermally insulating the annular heater from the base plate to maintain the temperature of the base plate substantially below the temperature of the tip of the sensor element, thereby causing an axial temperature gradient across the sensor element from the tip to the base thereof for increasing the potential difference generated by the sensor element when the probe is operating.

3. The probe of claim 1 wherein the catalyzing means comprises a coil having a plurality of turns of high nickel content wire.

4. The probe of claim 3 wherein the wire has a nickel content of approximately 80%.

5. The probe of claim 1, comprising four exit ports at 90-degree intervals around the base of the element and between the outer surface of the sensor element and the inner wall of the gas flow tube, for causing a radially uniform, axial flow of endothermic gas around the sensor element from the tip of the element to the base of the element.

6. An oxygen probe housing attachable to an auxiliary outlet of a heat treating furnace utilizing a replaceable oxygen sensor having a solid zirconium oxide electrolyte element comprising:
   a heat-conducting base plate defining an aperture around the oxygen sensor so that the sensor element protrudes through the center of the aperture, the base plate further having at least two substantially diametrically opposed exit ports extending therethrough and radially spaced from the center of the aperture for venting endothermic gas away from the area around the aperture;
   a gas flow tube having one end connected to the base plate so as to be coaxial with a line perpendicular to the base plate and passing through the center of the aperture, the inner wall of the tube enclosing the aperture and the exit ports, the other end of the gas flow tube having means for joining the gas flow tube to an auxiliary outlet of the furnace, the gas flow tube and the exit ports defining an axial, substantially radially symmetrical gas flow path around the sensor element, including means for catalyzing the endothermic gas within the gas flow tube to reduce soot deposits within the tube;
   a controllable annular heater having an inner surface contacting the outer wall of the gas flow tube and having one end towards the base plate and the remaining end extending away from the base plate approximately twice the length of the sensor element to locate the tip of the sensor element at approximately the midsection of the heater;
   means for measuring the temperature of the midsection of the heater and to determine the temperature of the tip of the sensor element; and
   means for maintaining the measured temperature of the sensor element tip greater than the temperature of the endothermic gas entering the gas flow tube.

7. The probe of claim 6, wherein the probe further includes means for thermally insulating the annular heater from the base plate to maintain the temperature of the base plate substantially below the temperature of the tip of the sensor element, thereby causing an axial temperature gradient across the sensor element from the tip to the base thereof for increasing the potential difference generated by the sensor element when the probe is operating.

8. The probe of claim 6 wherein the catalyzing means comprises a coil having a plurality of turns of high nickel content wire.

9. The probe of claim 8 wherein the wire has a nickel content of approximately 80%.

10. The probe of claim 6 comprising four exit ports at approximately 90-degree intervals between the aperture and the inner wall of the gas flow tube.

* * * * *